United States Patent

Kakimoto et al.

Patent Number: 5,319,094
Date of Patent: Jun. 7, 1994

[54] PROCESS FOR PRODUCING 2-ALKYL-4-HALO-5-FORMYLIMIDAZOLES

[75] Inventors: Takehiko Kakimoto, Gifu; Toshimi Ogawa, Ogaki, both of Japan

[73] Assignee: Nippon Gohsei Kagaku Kogyo Kabushiki Kaisha, Osaka, Japan

[21] Appl. No.: 999,134

[22] Filed: Dec. 31, 1992

Related U.S. Application Data

[63] Continuation of Ser. No. 872,076, Apr. 22, 1992, abandoned.

[30] Foreign Application Priority Data

Apr. 23, 1991 [JP] Japan .................. 3-187117

[51] Int. Cl.$^5$ .......................... C07D 233/64
[52] U.S. Cl. ................................ 548/341.5
[58] Field of Search ...................... 548/341.5

[56] References Cited

U.S. PATENT DOCUMENTS

| | | | |
|---|---|---|---|
| 4,207,324 | 6/1980 | Matsumura et al. | 518/337 |
| 4,810,828 | 3/1989 | Fenske et al. | 548/337 |
| 4,995,898 | 2/1991 | Nasu et al. | 548/337 |
| 5,023,336 | 6/1991 | Shigehara et al. | 548/337 |

*Primary Examiner*—Patricia L. Morris
*Attorney, Agent, or Firm*—Armstrong, Westerman, Hattori, McLeland & Naughton

[57] ABSTRACT

This invention provides a process for producing 2-alkyl-4-halo-5-formylimidazoles which includes halogenating 2-alkyl-5-formylimidazoles with a N-halosuccinimides in the presence of dioxane or mixture of dioxane and ethylene glycol monomethylether as solvent and in the presence of alkali metal hydrogen carbonate as catalyst, which are readily available, with good yield.

5 Claims, No Drawings

PROCESS FOR PRODUCING 2-ALKYL-4-HALO-5-FORMYLIMIDAZOLES

This application is a continuation-in-part of application Ser. No. 07/872,076, filed Apr. 22, 1991, now abandoned.

FIELD OF THE INVENTION

The present invention relates to a novel process for producing 2-alkyl-4-halo-5-formylimidazoles which are of value as starting compounds for medicaments such as diuretics and antihypertensive agents.

BACKGROUND OF THE INVENTION

2-Alkyl-4-halo-5-formylimidazoles are important chemicals as mentioned above and are, therefore, attracting much attention in recent years However, there is little information on relevant production technology. The only pertinent literature (Japanese Laid-open Patent Application No. 54-148788) known to the inventors of the present invention describes a production process starting with, for example, 2-amino-3,3-dichloroacrylonitrile and an aldehyde and involving the corresponding Schiff base as an inter mediate.

This technology is disadvantageous in that the starting material 2-amino-3,3-dichloroacrylonitrile is not easily available with the result that commercial production is remarkedly handicapped. Therefore, the industry has been aspiring to finding a new production process for 2-alkyl-4-halo-5-formylimidazoles which can give these compounds in good yield from starting materials which are readily available.

After intensive research, the inventors of the present invention discovered a novel route of synthesis which comprises halogenating an 2-alkyl-4-halo-5-formylimidazole with an N-halosuccinimide. The present invention is predicated on the above finding.

SUMMARY OF THE INVENTION

The present invention relates to a process for producing an 2-alkyl-4-halo-5-formylimidazole which comprises halogenating an 2-alkyl-5-formylimidazole with a N-halosuccinimide in the presence of dioxane or mixture of dioxane and ethylene glycol monomethyl ether as solvent and in the presence of alkali metal hydrogen carbonate as catalyst.

This process is schematically illustrated below.

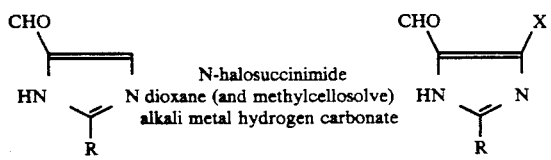

(wherein R means an alkyl group which preferably contains 2 to 6 carbon atoms and X is preferably chloro or bromo)

DETAILED DESCRIPTION OF THE INVENTION

Refferring to the starting compound 2-alkyl-5 formylimidazole, the alkyl group designated by R is a lower alkyl group preferably containing 2 to 6 carbon atoms. The halogen of the N-halosuccinimide is preferably chloro or bromo and the use of each kind of N-halosuccinimide gives rise to the corresponding 2-alkyl-4-halo-5-formylimidazole.

In practicing the process of the invention, such N-halosuccinimide is used in a proportion of 0.5 to 1.5 mols, preferably 1.0 to 1.15 mols, to each mole of the starting compound 2-alkyl-5-formylimidazole. This reaction can be carried out in the presence of a catalyst.

The solvent used for this reaction is limited to dioxane or mixture of dioxane and ethylene glycol monomethyl ether. The proportion of the solvent is limited by the solubility of the starting compound 2-alkyl-5-fromylimidazole but, for practical purposes, is preferably 5 to 20 times the proportion of the starting compound by weight. p The other solvents, for example, halogenated hydrocarbons such as methyl chloride, methylene chloride, chloroform, carbon tetrachloride, 1-chloroethane, 1,2-dichloroethane, etc., saturated hydrocarbons such as pentane, hexane, heptane, octane, etc., aromatic hydrocarbons such as benzene, toluene, xylene, etc., esters such as ethyl acetate, isopropyl acetate, etc., and ethers such as diethyl ether, dipropyl ether, etc., give low yield.

The catalyst used for this reaction is sodium hydrogen carbonate or potassium hydrogen carbonate. The proportion of the catalyst is 0.01 to 0.10 mol, preferably 0.03 to 0.05 mol, to each mol of the starting compound 2-alkyl-5-formylimidazole.

The mode of feeding is optional for any of the reactants. Thus, they can be fed to the reaction system all in one operation, in installments, continuously or dropwise. However, charging in one operation is advantageous.

The reaction temperature may range from 0° to 80° C. and is preferably 30° to 60° C. The reaction time is 0.5 to 12 hours and preferably 1 to 10 hours.

After completion of the reaction, the reaction mixture is concentrated under reduced pressure and the residue is dissolved in a suitable solvent. The solution is extracted with water and the top layer is separated and concentrated to give the object compound 2-alkyl-4-halo-5-formylimidazole. Where necessary, the compound is further purified by procedures well known to chemists.

It is noted that the separation from byproduct succinic acid from halogenated imidazoles can be accomplished rather easily.

The yield of the object compound is about 50 to about 80% of the starting compound 2-alkyl-5-formylimidazole.

The present invention is very advantageous, from industrial and economic points of view, in that 2-alkyl-4-halo-5-formylimidazoles, which are important starting materials for medicaments such as diuretics and antihypertensive agents, can be produced from readily available starting compounds with ease and good yield.

The following examples are further illustrative of the present invention.

Example 1

To a mixture of 36.0 g of dioxane was added 4.0 g (0.0263 mol) of 2-butyl-5-formylimidazole, 4.04 g (0.0303 mol) of N-chlorosuccin-imide and, as the catalyst, 0.11 g (0.001263 mol) of sodium hydrogen carbonate and the mixture was stirred at a constant temperature of 50° C. for 7.0 hours. After completion of the reaction, the reaction mixture was further ripened for 0.5 hours, after which it was concentrated under reduced pressure. To the residue were added ethyl acetate and water, and, after shaking, the upper layer was taken and concentrated to give 5 g of a black concentration residue. As analyzed by high performance liquid chromatography, the yield of the product was 75% based on the starting compound 2-butyl-5-formylimidazole consumed.

The product obtained above was dissolved in chlorobutane for recrystallization. The resulting crystals showed a melting point of 92°-95° C. in agreement with 2-butyl-4-chloro-5-formylimidazole.

Example 2

To a mixture of 23.0 g of dioxane and 13.0 g of methylcellosolve (ethylene glycol monomethyl ether) were added 4.0 g (0.0263 mol) of 2-butyl-5-formylimidazole, 4.04 g (0.0303 mol) of N-chlorosuccinimide and, as the catalyst, 0.11 g (0.001263 mol) of sodium hydrogen carbonate and the mixture was stirred at a constant temperature of 50° C. for 7.0 hours. After completion of the reaction, the reaction mixture was further ripened for 0.5 hours, after which it was concentrated under reduced pressure. To the residue were added ethyl acetate and water, and, after shaking, the upper layer was taken and concentrated to give 5 g of a black concentration residue. As analyzed by high performance liquid chromatography, the yield of the product was 60% based on the starting compound 2-butyl-5-formylimidazole consumed.

The product obtained above was dissolved in chlorobutane for recrystallization. The resulting crystals showed a melting point of 92°-95° C. in agreement with 2-butyl-4-chloro-5-formylimidazole.

Comparative Example 1

The procedure of Example 1 was repeated except that 36.0 g of the following solvent was used in lieu of 36.0 g of dioxane.

The yield of the concentration residue was about 10–30% based on the starting compound 2-propyl-5-formylimidazol consumed.

| Solvent used | Yield |
| --- | --- |
| Methyl chloride | 29% |
| Methylene chloride | 21% |
| Chloroform | 16% |
| Carbon tetrachloride | 20% |
| 1-Chloroethane | 15% |
| 1,2-Dichloroethane | 28% |
| Pentane | 12% |
| Hexane | 11% |
| Octane | 10% |
| Benzene | 11% |
| Toluene | 9% |
| Xylene | 9% |
| Ethyle acetate | 29% |
| Isopropyl acetate | 31% |
| Diethyl ether | 22% |
| Di-n-propyl ether | 14% |

Example 3

The procedure of Example 1 was repeated except that 2-propyl-5-formylimidazole and N-bromosuccinimide were used in lieu of 2-butyl-5-formylimidazole and N-chlorosuccinimide, respectively.

The yield of the concentration residue was 79% based on the starting compound 2-propyl-5-formylimidazol consumed. The residue was dissolved in isopropyl alcohol for recrystallization to give 2-propyl-4-bromo-5-formylimidazole.

Example 4

The procedure of Example 2 was repeated except that 2-propyl-5-formylimidazole and N-bromosuccinimide were used in lieu of 2-butyl-5-formylimidazole and N-chlorosuccinimide, respectively.

The yield of the concentration residue was 75% based on the starting compound 2-propyl-5-formylimidazol consumed. The residue was dissolved in isopropyl alcohol for recrystallization to give 2-propyl-4-bromo-5-formylimidazole.

Comparative Example 2

The procedure of Example 3 was repeated except that 36.0 g of the following solvent was used in lieu of 36.0 g of dioxane.

The yield of the concentration residue was 10–30% based on the starting compound 2-propyl-5-formylimidazol consumed.

| Solvent used | Yield |
| --- | --- |
| Methyl chloride | 33% |
| Methylene chloride | 21% |
| Chloroform | 17% |
| Carbon tetrachloride | 22% |
| 1-chloroethane | 15% |
| 1,2-Dichloroethane | 32% |
| Pentane | 12% |
| Hexane | 12% |
| Octane | 10% |
| Benzene | 11% |
| Toluene | 12% |
| Xylene | 13% |
| Ethyle acetate | 33% |
| Isopropyl acetate | 32% |
| Diethyl ether | 20% |
| Di-n-propyl ether | 16% |

What is claimed is:

1. A process for producing an 2-alkyl-4-halo-5-formylimidazole which comprises halogenating an 2-alkyl-5-formylimidazole with a N-halosuccinimide in the presence of dioxane or a mixture of dioxane and ethylene glycol monomethyl ether as a solvent and in the presence of an alkali metal hydrogen carbonate as catalyst.

2. The process of claim 1 wherein said alkyl is an alkyl group of 2 to 6 carbon atoms.

3. The process of claim 1 wherein said N-halosuccinimide is N-chlorosuccinimide.

4. The process of claim 1 wherein said N-halosuccinimide is N-bromosuccinimide.

5. A process for producing an 2-alkyl-4-halo-5-formylimidazole which comprises halogenating an 2-alkyl-5-formylimidazole with a N-halosuccinimide in the presence of dioxane or a mixture of dioxane and ethylene glycol monomethyl ether as a solvent.

* * * * *